United States Patent [19]

Schlensog et al.

[11] Patent Number: 4,673,388
[45] Date of Patent: Jun. 16, 1987

[54] BREAST PUMP

[75] Inventors: Klaus Schlensog, Cham; Christian Beer, Boniswil; Robert Riedweg, Lucerne, all of Switzerland

[73] Assignee: Ameda AG, Switzerland

[21] Appl. No.: 711,676

[22] Filed: Mar. 14, 1985

[30] Foreign Application Priority Data

Mar. 14, 1984 [CH] Switzerland .......................... 1268/84

[51] Int. Cl.$^4$ .............................................. A61M 1/06
[52] U.S. Cl. ...................................... 604/74; 604/346; 128/36
[58] Field of Search ...................... 604/73–76, 604/346; 119/14.37–14.39; 128/32, 34–36

[56] References Cited

U.S. PATENT DOCUMENTS

| 1,596,520 | 2/1922 | Eskholme et al. | 604/74 |
| 3,931,795 | 1/1976 | Duncan | 119/14.38 |
| 4,263,912 | 4/1981 | Adams | 604/75 |

FOREIGN PATENT DOCUMENTS

| 3,328,725 | 2/1984 | Fed. Rep. of Germany | 604/74 |
| 0158976 | 5/1957 | Sweden | 604/74 |
| 2082920 | 3/1982 | United Kingdom | 604/75 |
| 2127293 | 4/1984 | United Kingdom | 604/74 |

Primary Examiner—Dalton L. Truluck
Assistant Examiner—Mario Constantino
Attorney, Agent, or Firm—Fidelman & Wolffe

[57] ABSTRACT

The breast pump (1) for sucking off breast milk has a suction bell (10), which is intended to be laid against the breast and which is connected with a storage container (12) for pumped-off milk arranged at an angle to the longitudinal axis ($A^3$) of the suction bell and with a suction pump (15) driven by an electric motor (11), in order to produce sufficient suction for the pumping-off process inside the suction bell; the pump (1) has an attachment housing (18) which comprises two limbs (14, 16) connected to each other at an angle, which housing is connected in a detachable manner with the suction bell (10) and contains the electric motor (11), a low voltage current source (13) for the latter, for example, a battery or an accumulator, and the suction pump (15). The longitudinal axis ($A^1$) of one (14) of the limbs of the housing lies practically parallel to the longitudinal axis ($A^3$) of the suction bell (10) and the longitudinal axis ($A^2$) of the other limb (16) of the housing lies practically parallel to the longitudinal axis ($A^4$) of the storage container (12).

The new breast pump can be made of light and comparatively inexpensive parts and can be used as a compact entity similar to manual pumps, yet with the advantages of the mechanical drive. Possible vibrations act transverse to the mamilla axis and in general are felt to be beneficial and lactogenic.

4 Claims, 3 Drawing Figures

BREAST PUMP

Two types of breast pumps are common for artificially sucking off breast milk, said pumps basically differing from each other on account of the fact that the suction or the low pressure of between typically 50 and 400 mb required to allow the milk to flow out of the breast is either produced manually with, for example, a rubber ball or trunk piston operated by hand, or mechanically with, for example, an electric motor and a suction pump driven by the latter.

Breast pumps are required when the child has suckling difficulties (drinking weakness or mechanical sucking impediments), in the case of hypogalactia (for increasing the milk secretion) or hypergalactia (excessively tight breast or incomplete emptying), in the case of problematic breasts or breasts sore from suction (mamilla which are too small or sunken mamilla or injury of the mamilla), when the mother or child is temporarily ill and finally when the mother does not have or does'nt always have the necessary time for feeding.

Reasons for the generally growing importance attributed to artifically sucking off the breast milk by a pumping-off process, the problems encountered thereby and also manual and mechanical pumps usually used therefor have been examined and elucidated in recent years by Tibbetts, E. et al in the journal MCN, "Maternal Child Nursing", Volume 5 (Part: July–August 1980), pages 262-264. The EGNELL (registered trade mark) pump, which is described and recommended in this journal as an example of a mechanical pump, is typical of known modern mechanical pumps. It comprises a suction bell, which is intended to be laid against the breast and which is connected with a storage container for pumped-off milk arranged at an angle to the suction bell and with a pump driven by a sufficient electric motor, in order to produce sufficient suction for the pumping-off process inside the suction bell. Known pumps of this kind are driven by a motor for operation with mains current and are combined with the latter to form a pump/motor combination which is comparatively heavy, that is, which weighs 8-15 kg, which cannot be transported easily and which is connected with the handling unit, consisting of suction bell and storage container, by means of a hose.

The advantages of such mechanical breast pumps are the even suction, which may be varied cyclically if desired, and the fatigue-free operation, even with prolonged duration of the sucking-off process.

The disadvantages are, apart from the comparatively high costs, the heavy weight and also the space required for the motor/pump combination and the corresponding lack of transportability of lack of scope for handling as a whole.

The main advantage of the manual pumps is their cost, which by way of comparison is very much lower, and the little space they require; the disadvantages are the suction action, which is generally very uneven or insufficient, and also frequently an excessively high strain on the mamillary skin, because steadily holding the pump or suction bell with simultaneous pumping movements results in a more or less distinct dislocation of the mamilla axis ("bending-off" of the mamilla).

The combination of the handling unit (suction bell/storage container) of conventional motor-driven pumps with a light pump and a light low voltage current electric motor and also with a corresponding source of current offers itself as a general solution to the problems explained of the known motor-driven pumps, on the one hand, and of the manual pumps, on the other hand.

The experiments leading to the present invention revealed, however, that the use of small low voltage current motors with battery or accumulator supply and small pumps, such as vane-type pumps, bellows pumps or diaphragm pumps, leads to problems. These problems prefer to be so grave that such mechanical battery-operated breast pumps were assessed by test subjects to be not very useful and compared with the manual pumps to have more disadvantages than advantages.

In such tests, the poor weight distribution, the lack of stability and, more particularly, the effect of the vibration which is practically scarcely avoidable, were felt to be particularly disadvantageous.

The object of the invention is to specify a breast pump construction which is suitable for low voltage current operation and which, despite integral combination of low voltage current motor, low voltage current source and pump with the handling unit consisting of suction bell and storage container, offers a compact and light mechanical breast pump with a sufficiently low centre of gravity which preferably lies approximately in the vertical standing axis of the handling units, as a result of which vibrations which might result are not felt to be unpleasant, but stimulating.

The object is met according to the invention by means of a housing which comprises two limbs connected with each other at an angle, which is mounted in a detachable manner on the suction bell and which contains the electric motor, a low voltage current source for the latter and the pump, the longitudinal axis of one of the limbs of the housing and preferably even the axis of rotation of the electric motor lying practically parallel to the longitudinal axis of the suction bell and the longitudinal axis of the other limb of the housing lying practically parallel to the longitudinal axis of the storage container.

The housing of a pump according to the invention containing the motor, the pump and the low voltage current source is generally a removable attachment on the bend-containing suction bell/storage container unit and has practically identical and parallel bending or rather practically identical bending displaced in a parallel manner. The preferred bend angle in the suction bell/storage container unit results from the fact that the longitudinal axis of the storage container can be held advantageously so that it is approximately perpendicular when sucking-off, if the pump is used in a comfortable sitting position, that is, with the upper part of the body leaning back slightly, and typically amounts to 150°-90°, for example, approximately 120°. The range of tolerance amounts to approximately ±10°.

The motors, which can be used for operation with standard pocket-lamp batteries or corresponding single-cells and which have output in the typical range of 10-500 mW sufficient for the pumping-off process, during operation as a rule produce a perceptible, that is, a significant, level of vibration with typical frequencies in the range of approximately 50-500 hertz which—if at all—can only be reduced at great expense and correspondingly at increased cost or be absorbed through damping, so that it is no longer noticed upon contact with an appliance driven in this way.

In the applicant's experiments leading to the invention, it was found that a vibration lying in the frequency range mentioned is felt by most of the test subjects to be either not unpleasant or else to be pleasantly stimulating during the pumping-off process, if the oscillation acts approximately linearly, perpendicularly with respect to the mamilla axis.

Accordingly, suction pumps according to the invention with oscillatory movement, more particularly with movement reciprocating practically linearly, such as piston, bellows or diaphragm pumps, are preferred and are arranged sio that the oscillatory movement is directed approximately perpendicularly in respect of the longitudinal axis of the suction bell. Diaphragm pumps having a planar and for the most part approximately circular diaphragm made of elastomer, such as synthetic or natural rubber which are connected with an eccentric via a spigot formed thereon or attached thereto, are preferred for reasons of effectiveness and cost.

In order to produce sufficient suction inside the suction bell even with pump output which is comparatively low, that is, a low pressure of up to 0.4 bar in a sufficiently short period of time of typically 5–20 seconds, it is convenient to work out the volume to be sucked off so that it is not unnecessarily great, and/or to connect the interior space of the storage container with the interior space of the suction bell via a valve arrangement in such a way that the former can be uncoupled at least for a time in order to reduce the volume to be pumped off, by means, for example, of leaf or ball valves which under the effect of a low pressure in the direction of the low pressure source give rise to a closing action without preventing the following passage of milk.

The internal volume of the suction bell up to the connection region to the storage container is preferably not substantially greater than the internal volume of the storage container which typically has a capacity of 80–200 ml and a total internal volume of 100–400 ml.

The suction bell/storage container unit of pumps according to the invention is preferably constructed so that it is sterilisable in the usual manner, for example, by treatment with boiling water and substantially transparent and translucent for checking purity, filling and operation. Examples of suitable materials for the suction bell and storage container are heat-resistant, transparent thermoplastic, such as polycarbonates or/and mineral glass.

The attachment housing preferably consists of a polymer substance which is suitable for injection moulding treatment, but which need not be resistant to boiling water, as it contains the low voltage current motor, which is not normally specially encapsulated, and also the low voltage current source, which is also generally sensitive to water and is therefore removed before sterilisation. A typical example of a material for the attachment housing is ABS (acrylic-butadiene-styrene).

Commercially available products can be used for the positions to be accommodated inside the attachment housing, that is, low voltage current motors for operation with 1.5 to 15 volts and supply current sources and also small suction pumps, switches and the like.

The invention is elucidated in the accompanying drawings, with the aid of a preferred exemplary embodiment.

Figure 1:
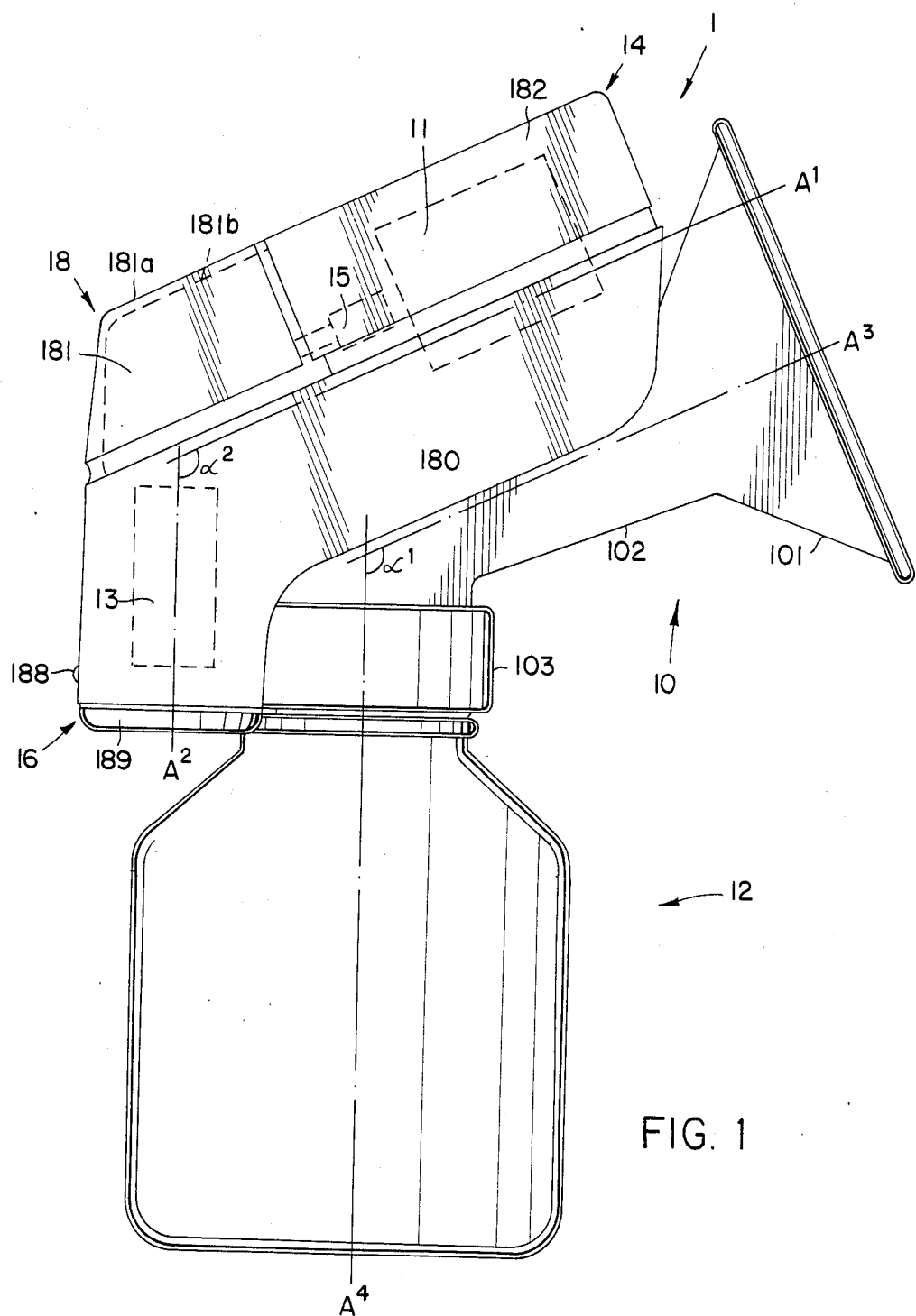
FIG. 1 shows the side view of a breast pump.

The breast pump 1 according to the invention, represented approximately to full scale in a side view in FIG. 1, consists of the elongate suction bell 10 which has a hollow conical end section 101 and a connecting section 102 which is also of hollow conical form, as described in greater detail in European patent application No. 83201846.9 belonging to the applicant.

The connection piece 103 is pre-formed on the connecting section 102 of the suction bell 10 at an angle $\alpha^1$ of 90°–150°, preferably approximately 120°, and renders possible simple connection of the storage container 12 by means, for example, of a bayonet-type or screw joint. The angle $\alpha^1$ is defined by the position of the longitudinal axis $A^3$ of the suction bell 10 relative to the position of the longitudinal axis $A^4$ of the storage container 12.

Figure 2:
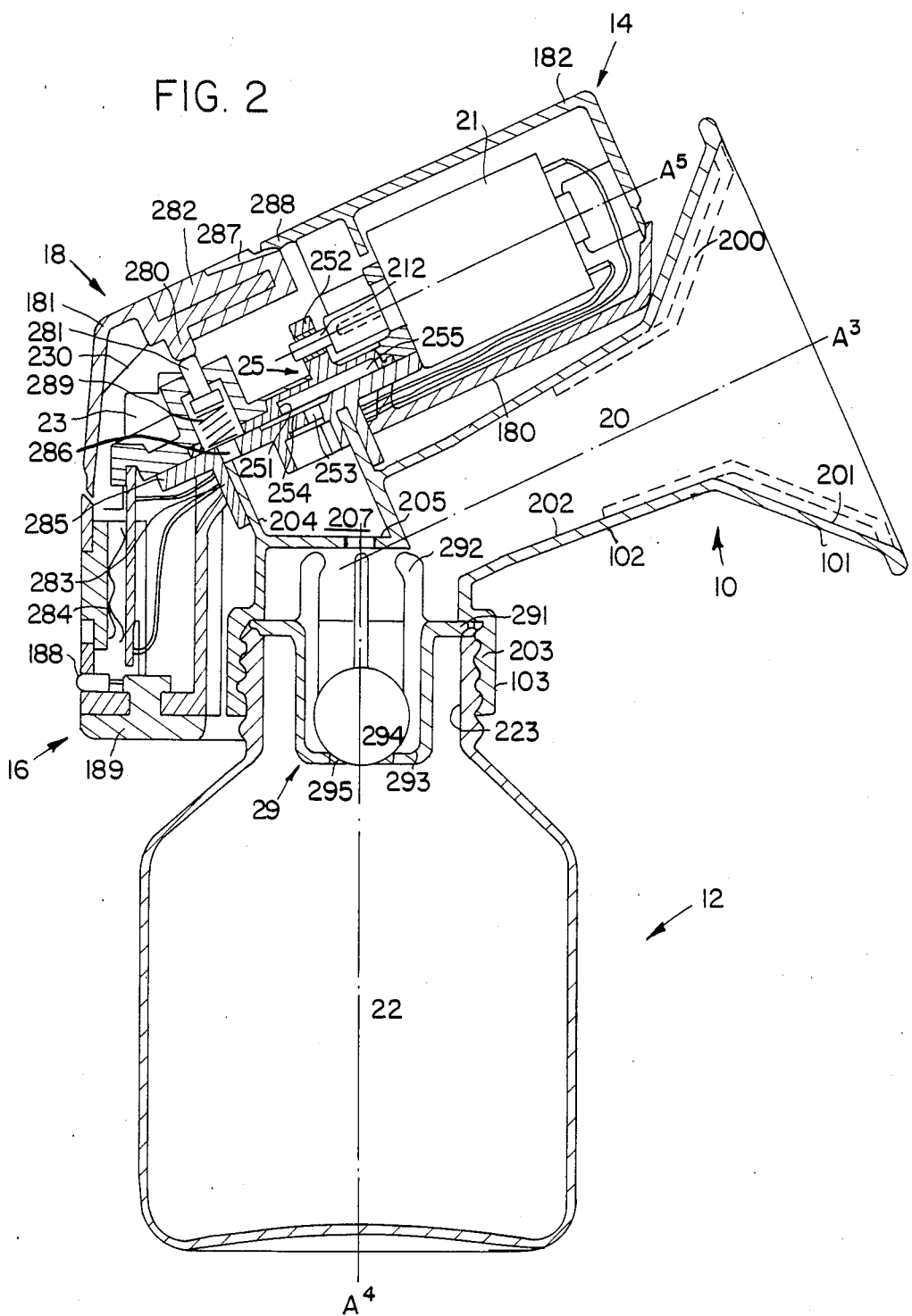
FIG. 2 shows the cross section through the breast pump shown in FIG. 1 in the plane defined by the longitudinal axes of suction bell and storage container and FIG. 3 shows the top view of the breast pump from FIG. 1.

The attachment housing 18 consists of two housing sections or limbs 14, 16, which are at an angle ($\alpha^2$) with respect to each other, and is connected in a detachable manner with the suction bell 10 in, for example, the manner explained further below (FIG. 2). The position of one of the limbs 14 of the housing is defined by its longitudinal axis $A^1$ which lies practically parallel (tolerance $\pm 10°$) to the longitudinal axis $A^3$ of the suction bell 10. The other limb 16 of the housing is defined by its longitudinal axis $A^2$ which lies practically parallel (tolerance $\pm 15°$) to the longitudinal axis $A^4$ of the container 12. The position of the longitudinal axes $A^1$, $A^2$ is defined by the centres of gravity of the cross-sectional areas belonging thereto.

According to FIG. 1 the housing 18 has a lower portion 180 and two cover portions 181, 182, one portion 181 of which may be moved like a press button and can be swung between the rest position 181a and the operating position 181b. This renders possible effortless suction control as explained further below. The base 189 of the second limb 16 can be constructed so that it is removable or capable of being swung off for simple exchange of the low voltage current source(s) 13.

The state of charging of the low voltage current source 13 can be checked in the operating state with the aid, for example, of a charge-monitoring lamp 188. As explained more thoroughly in the following with the aid of FIG. 2, the low voltage current motor 11 and the suction pump 15 driven by the latter are arranged inside the attachment housing 18 which embraces, partly forming an arch or like a saddle, the connecting portion 102 and the flange 103 of the suction bell 10.

The sectional view of the breast pump 10 shown in FIG. 2 corresponds to the plane defined by the axes $A^3$, $A^4$. The lower portion 180 has an approximately cylindrical attachment connection piece 283 which is mounted so that it fits tightly on the connection piece 204 which, for its part, is pre-formed on the suction bell 10 in the region of the knee-bend between the connecting portion 102 and the connection piece 103.

The connection piece 283 is part of a support plate 285 which has an opening 253 for one-way connection with the suction chamber 255 of the pump 25 and a second opening 286 for one-way connection with the atmosphere.

The low voltage current motor 21 is mounted in the first limb 14 of the housing 18, that is, in the limb approximately parallel to $A^3$, in such a way that the rotational axis $A^5$ lies approximately parallel (tolerance $\pm 5°$) to the axis $A^3$.

The eccentric 212 of the motor 21 engages into the oscillating control piston 252 of the flexible diaphragm 251 of the diaphragm pump 25. The chamber 255 of the pump 25 is connected, on the one hand, (in a manner not shown) with the atmosphere and, on the other hand, by way of the flutter valve 254 and the opening 253 with the chamber 207, which is formed by the feed pipe 204 of the suction bell 10 and the plate 285 of the connection piece 283 and has on its lower side a base wall 209 which by means of the opening 205 is connected with the interior space 20 of the suction bell 10.

Arranged in the second limb 16 of the attachment housing is the low voltage current source 23, in this case two single-cells (only the rear cell drawn) which are electrically connected with the motor 21 via a sliding switch 284 and which can be drawn out downwards after the base 189 has been swung off.

The button-like, movable portion 181 of the attachment housing 18 has a slide 282 with an oblique end surface whose relative position with respect to the adjacent edge of the lid portion 182 determines the rest position of the lid portion 181 and therewith the position of the projection 280 which, in its turn, acts on the suction control valve 281.

The connection piece 103 has, for the purposes of connection with the container 12, an internal thread 203 which fits onto the external thread 223 of the container 12. A plate 291 made of elastic material, serving, on the one hand, as a seal between the suction bell 10 and the container 12 and, on the other hand, as a support for the valve arrangement 29, is set or screwed into the connection piece 103.

The valve arrangement 29 consists of a bowl-like lower portion 293 which accommodates a ball valve 294 and whose base has a circular opening 295. From the plate 291 there project upwards several prongs 292 which prevent the ball 294 from falling out of the overall arrangement 29. The ball 294 closes the opening 205 at the upper end of its, the ball's path. The ball 294 is such (volume/weight) that it is lifted upwards when the container 12 is overfilled by the rising level of milk until the opening 205 is closed and then prevents both further sucking-off from the breast and sucking-in of milk into the chamber 207. The valve arrangement 29 can also be constructed, alternatively or additionally, in such a way that in the event of temporary interruption of suction through opening of the valve 281, the evacuated interior space 22 is uncoupled, that is, remains further under low pressure and thus reduces the air volume to be pumped off anew.

The breast pump 1 can be operated as follows:

The suction bell 10 with storage container 12 screwed thereon and housing 18 mounted thereon is laid against the breast to be pumped off in such a way that the axis of the mamilla coincides approximately with the axis $A^3$, as a result of which the conical inner surface 201 is pressed lightly against the breast concentrically surrounding the areola. For adaptation to small breasts an insert 200 can be used as known per se for breast pumps from, for example, the European patent application cited above.

The switch 284 is now operated for the purposes of connecting the weak current source 23 with the motor 21. The cam 212 produces a movement of the piston 252, oscillating approximately linearly, practically perpendicularly with respect to the axis $A^3$ of the suction bell. Both possible vibration resulting from imbalance of the motor 21 and the vibration caused by oscillatory operation of the diaphragm pump 25 act practically perpendicular with respect to the axis $A^3$ and thereby also perpendicularly with respect to the mamilla axis, most of the test subjects finding this to be pleasantly stimulating and in general, in any case, not to be unpleasant.

As a result of the oscillatory movement of the piston 252, the diaphragm 251 is deformed for alternating enlargement and reduction of the chamber 255 and as a result, suction is produced under the action of the flutter valve 254 acting on the interior space 20 of the suction bell 10 through the opening 253 via the chamber 207 and also the opening 205, that is, a low pressure of between typically 0.05 and 0.4 b, more particularly of approximately 0.3 b, is produced.

The milk, sucked off as a result of the low pressure in the space 20, flows on the inner surface 202 or sprays against the outer side wall of the chamber 207 and runs downwards past the ball valve into the interior space 22 of the storage container 12 where it collects.

If the suction acting on the breast is felt to be too great, the cover portion 181 can be pressed downwards, whereby the projection 280 presses the valve 281 downwards against a spring 289 and thereby connects the chamber 207 with the atmosphere through the opening 286. The ball valve 294 is drawn downwards by the low pressure in the interior space 22 of the container and closes the opening 295.

When the cover portion 181 is released, the spring 289 or/and an auxiliary spring 230 press the valve 281 and the projection 280 upwards. In order to adjust the suction so that it is weaker, the slide 282 is shifted to the right and the inclined surface 287 is thereby shifted underneath the edge 288, the rest position of the projection 280 and accordingly of the valve 281 being displaced downwards. In this way, a secondary air current, which may be controlled by adjusting the slide 282, can reach the chamber 207 through the opening 286 and the suction acting through the opening 205 can be reduced to a level which is felt to be pleasant. The valve 281 can thus serve selectively to achieve a periodically fluctuating or/and a constant suction action below the suction maximum which may be achieved with the pump 25.

After the pumping-off process, the whole breast pump along with the attachment can be put down on a base and is advantageously stable owing to the favourable mass distribution of the breast pump according to the invention even when the container 12 is empty or not very full.

In order to use the pumped-off milk, the storage container 12 is screwed off and either emptied into another container or provided with a stopper (not shown) or suction rubber teat attachment and kept or used for feeding.

The suction bell 10 can be cleaned or sterilised separately, apart from the attachment 18, in the usual way and after combination with the attachment 18, in the usual way, and after the container 12 has been screwed on is again ready for the pumping-off process.

Figure 3:
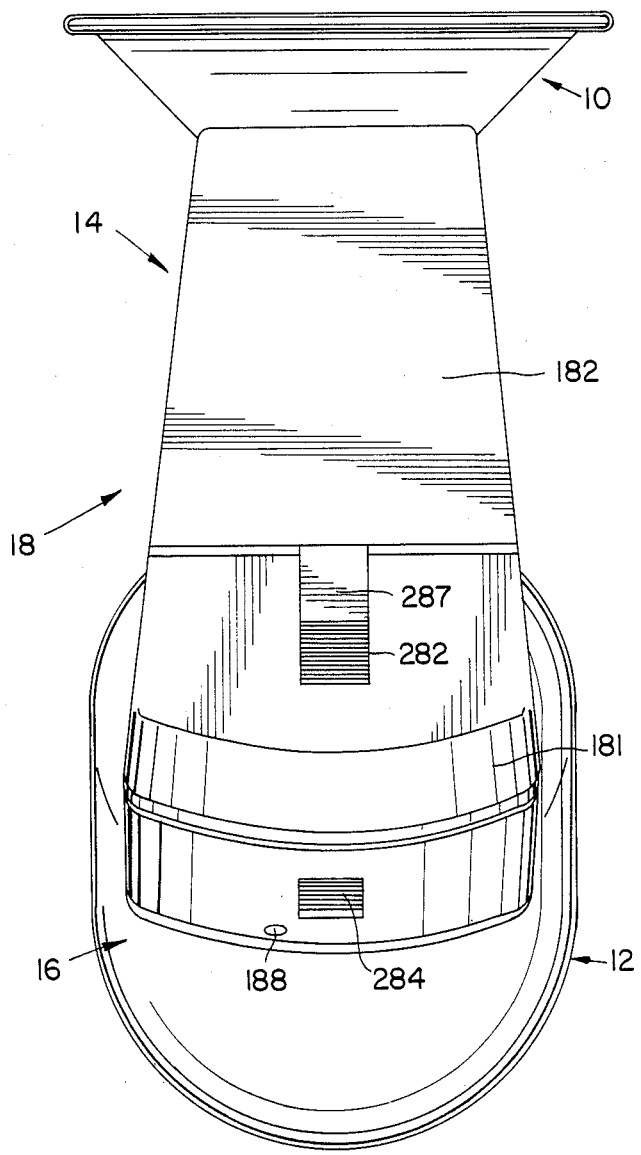

FIG. 3 shows a top view of the breast pump shown in FIG. 1; the test subjects assessed the arrangement of the suction control, that is, the lid portion 181 acting like a key and the slide 282 on the upper side of the attachment housing 18, to be particularly advantageous.

We claim:
1. In a breast pump having:
   a suction bell means for contact with a mother's breast, said suction bell means having a longitudinal axis;

a container means for receiving pumped-off milk detachably connected with said suction bell means, said container means having a longitudinal axis that intersects with the longitudinal axis of said suction bell means at an angle in the range of 90°–150°;

a suction pump means unit for reducing the pressure within said suction bell means, said suction pump means unit including a suction pump, an electric motor driving said suction pump and an electric battery operating said electric motor, the improvement comprising:

a first elongated housing of said pump means unit having a longitudinal axis substantially parallel to the longitudinal axis of said suction bell means and a second elongated housing having a longitudinal axis substantially parallel to the longitudinal axis of said container means;

said motor being disposed within said first longitudinal housing in axial alignment with the longitudinal axis thereof;

said suction pump also being disposed within said first longitudinal housing and comprising means for imparting a resultant linear oscillatory motion substantially perpendicular to the longitudinal axis of said suction bell means;

said battery being disposed within said second housing, the center of gravity of said breast pump being approximately aligned with the longitudinal axis of said container means; and valve means arranged intermediate said suction bell means and said container means for closing communication between said suction bell means and said container means operative to maintain reduced pressure within said container means when said suction bell means is temporarily held at atmospheric pressure.

2. The improvement of claim 1 further comprising a suction reducing by-pass valve fluidwise connecting said suction bell means to atmosphere, and a movable housing portion adapted to operate said valve, whereby manually pressing upon said movable portion of said housing may reduce the suction within said suction bell means.

3. The improvement of claim 2 further comprising slide means, cooperating with said movable housing portion, for fixing said suction reducing by-pass valve in position.

4. The improvement of claim 1 further comprising a chamber intermediate said valve means and said suction pump, an opening in said chamber being sealed by said valve means when said container means is filled with pumped-off milk, thereby preventing aspiration of milk into said suction pump.

* * * * *